United States Patent [19]

Martinello

[11] Patent Number: 5,083,464
[45] Date of Patent: Jan. 28, 1992

[54] PROCESS FOR TESTING IN SITU THE COMPRESSION STRENGTH OF CONCRETES OR THE LIKE AND THE AUTOMATIC APPARATUS TO PUT THE PROCESS INTO PRACTICE

[75] Inventor: Settimo Martinello, Bolzano, Italy
[73] Assignee: 4 Emme S.r.l., Bolzano, Italy
[21] Appl. No.: 567,969
[22] Filed: Aug. 15, 1990
[30] Foreign Application Priority Data
Nov. 13, 1989 [IT] Italy .................. 22371 A/89
[51] Int. Cl.⁵ .............................. G01N 3/00
[52] U.S. Cl. .......................... 73/803; 374/53
[58] Field of Search ............ 73/803, 821; 374/53
[56] References Cited
U.S. PATENT DOCUMENTS
3,974,679  8/1976 Nasser .................. 73/803 X
4,566,806  1/1986 DeBondt .................. 374/53

Primary Examiner—Jerry W. Myracle
Attorney, Agent, or Firm—Darby & Darby

[57] ABSTRACT

It is described a process and an apparatus in which the cure of the concrete is accelerated by raising the temperature and moisture values in the environment in which the cure is taking place. The process comprises the following steps: making up at least a test piece obtained through the casting of a predetermined amount of concrete to be tested into a hollow mold; introducing the made up test piece into a vessel; adjusting the chemico-physical parameters of the environment in the vessel, following predetermined operating steps; operating a device adapted to measure the compression strength of the test piece, which brings about the generation of signals depending upon the measured compression strength; processing and displaying the signals.

16 Claims, 1 Drawing Sheet

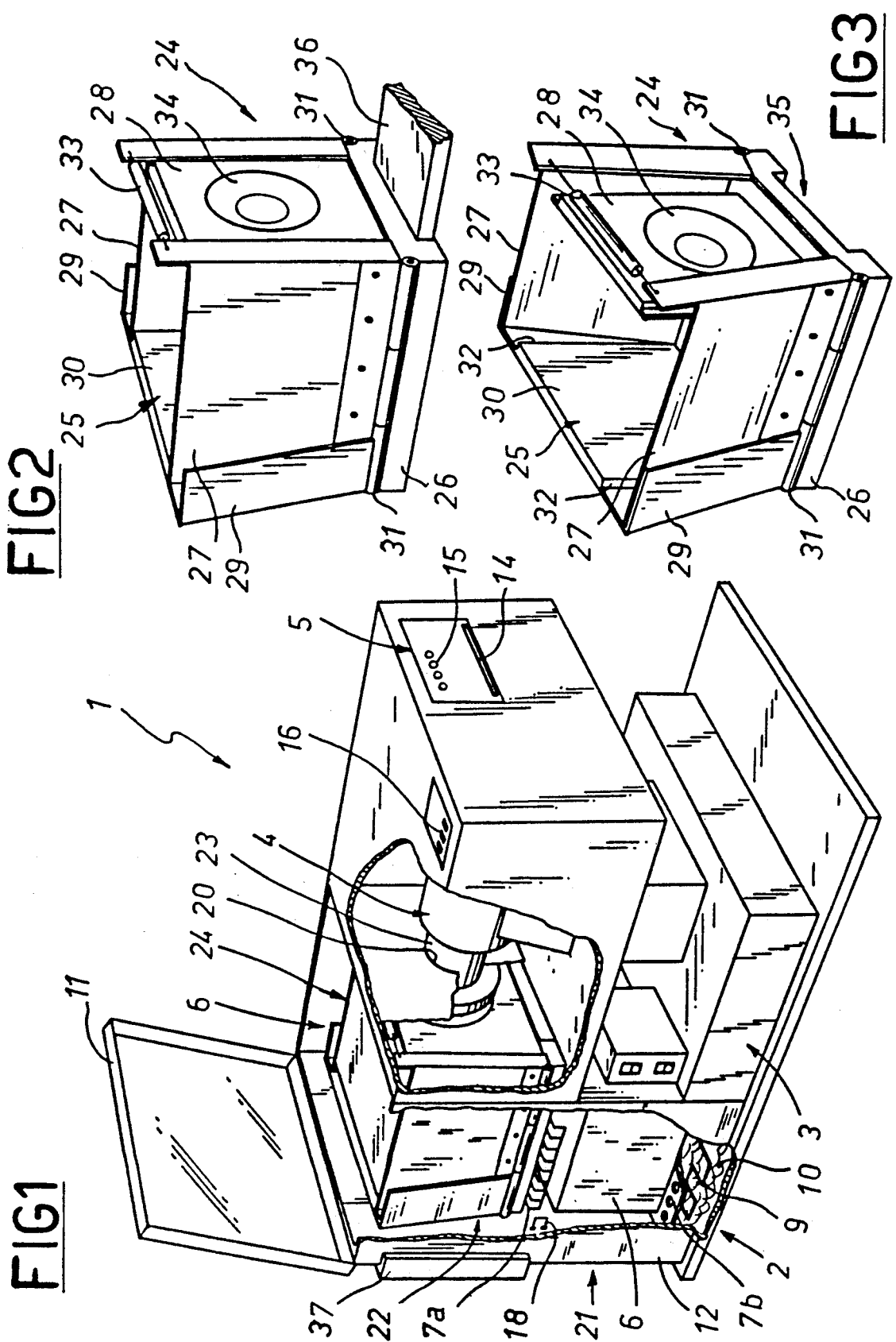

PROCESS FOR TESTING IN SITU THE COMPRESSION STRENGTH OF CONCRETES OR THE LIKE AND THE AUTOMATIC APPARATUS TO PUT THE PROCESS INTO PRACTICE

FIELD AND BACKGROUND OF THE INVENTION

The present invention relates to a process for testing in situ the compression strength of concretes or the like, and to an automatic apparatus to put the process into practice.

This type of apparatus is particularly used in the building field for testing the compression strength, also referred to as "characteristic strength", of concretes used in forming building structures.

As regards technical rules effective in Italy in the building field, a concrete is individualized on the basis of its characteristic compression strength which is defined as the compression strength value under which 5% of the population of all measured strength values is expected to be found. According to the Italian rules by "characteristic strength" it is meant to designate the strength resulting from compression tests carried out after a lapse of 28 days from the moment of the concrete casting on cube-shaped test pieces.

Therefore, following the traditional method pursuant to the rules presently in force in Italy it is possible to test the characteristic strength of the concrete used in a building only when twenty-eight days have elapsed.

Consequently this method involves the risk that when the concrete has already hardened, due to the result of the compression test the quality of the concrete must be degraded, or strengthening works are required or even the construction must be pulled down.

It is known that an increase in temperature in the case of the concrete represents a hardening accelerating factor, provided that the concrete is kept in a moist environment.

This knowledge is widely used in the industrial field for accomplishing small-sized manufactured articles and precast elements which are allowed to cure in heated environments having a high degree of moisture.

For the purpose, an apparatus has been devised which is the subject matter of the Italian patent application No. 84933/A87. The object of this application is an apparatus comprising: a cure furnace the inner environment of which has adjustable chemico-physical parameters; a transducer adapted to measure the temperature inside the furnace vessel and to emit a signal depending upon the detected value; a device for displaying all data detected by the transducer; a mechanical press adapted to load the test pieces to a predetermined value; a transducer designed to measure the pressure exerted by the mechanical press and emit a signal depending on the detected value; a processor associated with the transducers and capable of instantaneously supplying the value of the compression strength of the concrete and adjusting the temperature value within the vessel. In particular, the furnace and mechanical press in this apparatus consist of two separate devices so that at the end of the cycle an operator is needed for positioning the test piece under the press.

While this apparatus is very precise and reliable, it has the drawback that it needs the presence of an operator at the end of the cure cycle. In fact a cure protracted beyond the stated period modifies the results obtained since only the cure (breakage of the cube) carried out exactly at the end of the cycle can give a result which is the closest to the exact one.

SUMMARY OF THE INVENTION

The main object of the present invention is therefore to eliminate the above drawbacks by providing a process for testing the compression strength in situ of concretes within very short lapses of time, in the range of 24 hours from the casting, as well as the apparatus for putting the process into practice, both being excellent in operation and very reliable in the achieved results and, with reference to the apparatus, of simple construction, reduced bulkiness and relatively low prices.

Another object of the invention is to provide a process and an apparatus adapted to automatically complete the cure cycle with the breakage of the cube so as to always give excellent results, while not requiring the presence of an operator at the end of the cycle.

A still further object of the invention is to ensure that the applied force in order to achieve the breakage of the cube is perfectly perpendicular and acts on the whole concerned cube surface.

The foregoing and further objects are all attained by the process for testing in situ the compression strength of concretes or the like, in which the cure of the concrete is accelerated by raising the temperature and moisture values in the environment where said cure is taking place, which comprises the following operating steps:
  making up at least a cube or test piece obtained through the casting of a predetermined amount of concrete to be tested into a hollow mold;
  introducing said made up test piece into a vessel;
  adjusting the chemico-physical parameters of the environment in said vessel, following predetermined operating steps;
  operating a device adapted to measure the compression strength of said test piece, which brings about the generation of signals depending upon the measured compression strength;
  processing and displaying said signals.

The process in question is accomplished by an automatic apparatus comprising: a cure vessel exhibiting adjustable chemico-physical parameters and into which a test piece obtained through the casting of a predetermined amount of concrete to be tested, is introduced; a transducer for measuring the temperature within said vessel and emitting a signal depending upon the detected value; a device for displaying the data detected by said transducer; a mechanical press communicating with said vessel and designed to load said hollow mold containing said test piece to a predetermined value; at least a transducer adapted to measure the pressure exerted by said mechanical press and emit a signal depending upon the detected value; a processor associated with said transducers for instantaneously supplying the compression strength value of the concrete and adjusting the temperature value within the vessel.

BRIEF DESCRIPTION OF THE DRAWINGS

Further features and advantages of the invention will become more apparent from the following detailed description of one embodiment of the process and the preferred embodiment of the apparatus, given hereinafter by way of non-limiting example with reference to the accompanying drawings showing the apparatus, in which:

FIG. 1 is a perspective view of the automatic apparatus for putting the process of the invention into practice, certain parts being removed in order to render others more prominent;

FIG. 2 is a perspective view of the hollow mold in a closed position;

FIG. 3 is a perspective view of the hollow mold in an open position.

DESCRIPTION OF THE PREFERRED EMBODIMENT

Referring to the drawings, reference numeral 1 generally denotes an automatic apparatus for testing the compression strength of concrete in accordance with the process of the invention.

The apparatus 1 substantially consists of an electric furnace 2, a hydraulic gearbox 3, a hydraulic press 4 and a control group 5.

The electric furnace 2 is comprised of a box-shaped vessel 12, provided at the top with a lid 11 designed to permit access to the furnace 2.

Installed inside the furnace 2, at the lower part 21 thereof, is a heat exchange coil 9, above which two horizontal metal grids 7a and 7b are detachably engaged to the inner walls of the vessel 12. The grids 7a and 7b, designed to support the test pieces 6, are suitably spaced apart from each other in order to allow several test pieces 6 to be located inside the furnace. The heat exchange coil 9 is plunged in a water layer 10 for the purpose of creating the desired temperature and moisture conditions.

Associated with the furnace 2 is also a transducer 18 for temperature detection.

At its upper inner part 22, the furnace 2 exhibits an opening 20 adapted to communicate a rod 23 of the press 4 to the test piece 6 disposed on the upper grid 7a.

The test piece 6 is formed by casting a predetermined amount of concrete to be tested into a hollow mold 24. The hollow mold 24, substantially in the form of a parallelepiped, is open at the top and exhibits one rear wall 25 integral to a base plate 26, a second and a third side walls 27, hinged to the base plate 26, and a fourth front wall 28 movable relative to the first, second and third walls 25, 27.

The rear wall 25 has two stop wings 29 and exhibits a central area in which the thickness is greater than that of the wings 29.

The rotation of the side walls 27 about hinges 31 is limited towards the inside of the hollow mold 24 by the steps 32 resulting from the above difference in thickness exhibited by the rear wall 25, and towards the inside by the wings 29. The walls 27 are kept to their "closed" position shown in FIG. 2 by a spring 33.

The front wall 28 of greater thickness is held in a vertical position as shown in FIG. 2 by the side walls 27. Said wall 28 externally has a recessed portion 34 adapted to ensure the correct point of application of the pressure force exerted by the rod 23 on the wall 28 itself.

The base plate 26 has a longitudinal guide housing 35 located at the lower part thereof towards the outside of the hollow mold 24 and disposed parallelly to the side walls 27. This housing can be fitted on a rail 36 associated with the upper grid 7a and disposed parallelly to the advance direction of the rod 23 of the press 4. The coupling between the rail 36 and the guide housing 35 ensures that the rod 23 can carry out a perfect perpendicular action on the walls 25, 28.

Obviously at the position corresponding to the hollow mold 24 located on the grid 7a the furnace 2 is reinforced by plates 37 adapted to support the action of the press 4 on the test pieces 6.

The hydraulic part of the apparatus 1 is not described herein as it is known per se and conventional.

The hydraulic gearbox 3 controls the press 4 to which it is connected through hydraulic pipelines (not shown).

The control group 5 is located by the press 4 and it consists of an processor (not shown) with which a printer 14, a luminous display 15 and control pushbuttons 16 are associated.

Operation of the apparatus according to the invention described above mainly as regards structure, is as follows.

When the casting is being carried out, from the concrete it is drawn the amount necessary to make two cube-shaped test pieces 6 with the use of two hollow molds 24. The concrete to be tested is then cast into the hollow molds 24 which subsequently are placed into the furnace 6, the first one on the lower grid 7b —and during this operation the grid 7a is kept in a raised position, and the second one on the grid 7a.

Previously the lower part of the furnace 12 has been partially filled with an amount of water 10 sufficient to create the relative requested moisture at normal temperatures.

The furnace is then hermetically sealed.

At this point, by acting on the pushbuttons 16 the apparatus 1 is operated.

The optimal thermal cycle is then piloted by the control group 5 which suitably feeds the coil 9 according to predetermined steps.

The parameter adjusting step lasts less than 24 hours.

The value of the environmental moisture is kept constant during the parameter adjusting step and corresponds to about $80 \div 100\%$ of relative humidity.

During the different steps of the thermal cycle the luminous display 15 displays the instantaneous temperature, the elapsed time and the time still needed; at the end of the cycle it informs the operator, through a luminous signal, that the cubes 6 have completed cure. In addition, at the end of the thermal cycle the press 4 is automatically operated so that it breaks the test piece 6 located on the upper grid 7a. The value of the compressive strength thereof appears at the exit of printer 14.

The printer 14 itself can also be used to trace out the development of the temperature inside the furnace 2 during the different steps of the thermal cycle.

The apparatus 1 can be advantageously mounted on a suitable transport means capable of facilitating the transferring thereof to the use places.

Obviously in pratical use the apparatus for carrying out the process of the invention may take forms and configurations different from the one described above, without however departing from the protection scope of the invention. In addition all of the details can be replaced by technically equivalent elements and the shapes, sizes and materials used can be of any nature depending upon requirements, as well as it will be possible to vary the chemico-physical parameters within the limits of the inventive idea.

What is claimed is:

1. A process for testing compression strength of concrete, comprising the steps of:

accelerating curing of a sample by adjusting chemico-physical parameters of an environment within a vessel, the sample being of concrete which is cast and whose compression strength is to be tested;

compressing the sample within the vessel; and measuring compression strength of the sample as the sample is being compressed within the vessel.

2. A process as in claim 1, further comprising the step of breaking the sample as the curing of the sample becomes completed.

3. A process as in claim 2, further comprising indicating a value of the compressive strength of the sample.

4. A process as in claim 1, further comprising the steps of displaying instanteous temperature within the vessel, displaying elapsed time and time still need for completing curing, and indicating when curing is complete.

5. A process as in claim 1, wherein the step of accelerating includes raising temperature and moisture content within the vessel so as to accelerate the curing.

6. A process as in claim 5, further comprising tracing out a development of the temperature which is inside the vessel.

7. An apparatus for testing compression strength of concrete, comprising:

means for accelerating curing of the sample by adjusting chemico-physical parameters of an environment within a vessel, the sample being of concrete which is cast and whose compression strength is to be tested;

means for compressing the sample within the vessel; and means for measuring compression strength of the sample as the sample is being compressed within the vessel.

8. An apparatus as in claim 7, wherein said compressing means includes means for breaking the sample as the curing of the sample becomes completed.

9. An apparatus as in claim 7, further comprising means for displaying instanteous temperature within the vessel, means for displaying elapsed time and time still need for completing curing, and means for indicating when curing is complete.

10. An apparatus as in claim 7, wherein said accelerating means includes means for raising temperature and moisture content within the vessel so as to accelerate the curing.

11. An apparatus as in claim 10, further comprising means for tracing out a development of the temperature which is inside the furnace.

12. An apparatus as in claim 7, further comprising means for indicating a value of the compressive strength of the sample.

13. An apparatus as in claim 7, wherein said compressing means includes a mechanical press in communcation with the vessel for exerting compressive forces on the sample within the vessel.

14. An apparatus as in claim 7, further comprising a hollow mold within the vessel and into which is the sample, said mold having a base plate and first and second walls hingably connected to said base plate.

15. An apparatus as in claim 14, wherein said hollow mold has a third wall integral with said said base plate and has a fourth wall movable in response to said compression means relative to said first, second and third walls.

16. An apparatus as in claim 15, wherein said compressing means includes a movable rod, said base plate having a guide housing, further comprising a rail; and means for guidably coupling said guide housing to said rail for ensuring that the rod acts perpendicular to said third and fourthh walls for effecting the compressing.

* * * * *